United States Patent [19]
Baltz et al.

[11] Patent Number: 5,871,983
[45] Date of Patent: Feb. 16, 1999

[54] GLUCOSYLTRANSFERASE GENE GTFE FROM AMYCOLATOPSIS ORIENTALIS

[75] Inventors: Richard H. Baltz; Patricia J. Solenberg, both of Indianapolis; Patti J. Treadway, Greenwood, all of Ind.

[73] Assignee: Eli Lilly and Company, Indianapolis, Ind.

[21] Appl. No.: 926,258

[22] Filed: Sep. 5, 1997

Related U.S. Application Data

[60] Provisional application No. 60/026,055 Sep. 13, 1996.
[51] Int. Cl.$^6$ .............................. C12N 9/10; C12N 1/20; C12N 15/00; C07H 21/04
[52] U.S. Cl. .................. 435/172.3; 435/193; 435/252.3; 435/254.11; 435/320.1; 435/325; 435/410; 536/23.2; 935/22; 935/55
[58] Field of Search ................................. 435/172.3, 193, 435/254.11, 252.3, 325, 410, 320.1; 536/23.2; 935/22, 55

[56] References Cited

PUBLICATIONS

S. K. Chung, et al. "Biosynthetic Studies f Aridicin Antibiotics: Microbial Transformations and Glycosylations by Protoplasts." *Journal of Antibiotics* 39(5):652–659 (1986).

M. J. Zmijewski, Jr., and B. Briggs. "Biosynthesis of vancomycin: identification of TDP–glucose: aglycosyl–vancomycin glucosyltransferase from *Amycolatopsis orientalis.*" *FEMS Microbiology Letters* 5:129–134.

M. J. Zmijewski, Jr., and J. T. Fayerman. *Genetic and Biochemistry of Antibiotic Production* Ed. L.c. Vining and C. Stuttard. Butterworth Heinemann, Boston. Chapter 18: "Glycopeptide Antibiotics." pp. 71–83.

*Primary Examiner*—Rebecca E. Prouty
*Assistant Examiner*—Einar Stole
*Attorney, Agent, or Firm*—Thomas D.. Webster; David E. Boone

[57] ABSTRACT

The invention provides isolated nucleic acid compounds encoding a glycosyltransferase enzyme of *Amycolatopsis orientalis*. Also provided are vectors carrying genes that encode said enzyme, transformed heterologous host cells for expressing said enzyme, and methods for producing glycopeptide compounds using the cloned genes that encode said enzyme.

13 Claims, 2 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1224 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..1224

( x i ) SEQUENCE DESCRIPTION: SEQ ID NO:1:

```
ATG  CGT  GTG  TTG  TTG  TCG  ACC  TGT  GGG  AGC  CGC  GGA  GAC  GTC  GAA  CCA         4 8
Met  Arg  Val  Leu  Leu  Ser  Thr  Cys  Gly  Ser  Arg  Gly  Asp  Val  Glu  Pro
 1                 5                            10                           15

CTG  GTG  GCG  TTG  GCG  GTG  CGG  TTG  CGG  GAG  CGC  GGC  GCC  GAG  GTG  CGG         9 6
Leu  Val  Ala  Leu  Ala  Val  Arg  Leu  Arg  Glu  Arg  Gly  Ala  Glu  Val  Arg
```

-continued

|  |  |  |  | 20 |  |  |  | 25 |  |  |  | 30 |  |  |  |  |
|---|---|---|---|---|---|---|---|---|---|---|---|---|---|---|---|---|
| ATG | TGC | GCG | CCG | CCG | GAC | TGC | GCG | GAT | CGG | CTG | GCC | GAA | GTC | GAC | GTG | 144 |
| Met | Cys | Ala | Pro | Pro | Asp | Cys | Ala | Asp | Arg | Leu | Ala | Glu | Val | Asp | Val |  |
|  |  | 35 |  |  |  |  | 40 |  |  |  |  | 45 |  |  |  |  |
| CCG | CAT | CTG | CCC | CTC | GGT | GCG | TCG | GCC | CGC | CCG | TCG | GCC | GGG | CAG | GCG | 192 |
| Pro | His | Leu | Pro | Leu | Gly | Ala | Ser | Ala | Arg | Pro | Ser | Ala | Gly | Gln | Ala |  |
|  |  | 50 |  |  |  |  | 55 |  |  |  |  | 60 |  |  |  |  |
| AAA | CCC | TTG | ACG | GCC | GAG | GAC | ATG | CTC | CGG | TTC | ACG | ACC | GAG | ACG | ATC | 240 |
| Lys | Pro | Leu | Thr | Ala | Glu | Asp | Met | Leu | Arg | Phe | Thr | Thr | Glu | Thr | Ile |  |
| 65 |  |  |  |  | 70 |  |  |  |  | 75 |  |  |  |  | 80 |  |
| GCC | ACG | CAG | TTC | GAG | CGG | ATT | CCG | GCG | GCC | GCC | GAA | GGA | TGC | GCC | GCG | 288 |
| Ala | Thr | Gln | Phe | Glu | Arg | Ile | Pro | Ala | Ala | Ala | Glu | Gly | Cys | Ala | Ala |  |
|  |  |  |  | 85 |  |  |  |  | 90 |  |  |  |  | 95 |  |  |
| GTG | GTG | ACG | ACC | GGC | CTG | CTG | GCC | GCC | GCC | ATC | GGC | GTG | CGG | TCG | GTG | 336 |
| Val | Val | Thr | Thr | Gly | Leu | Leu | Ala | Ala | Ala | Ile | Gly | Val | Arg | Ser | Val |  |
|  |  |  | 100 |  |  |  |  |  | 105 |  |  |  |  | 110 |  |  |
| GCC | GAA | AAG | CTG | GGC | ATC | CCC | TAC | TTC | TAT | GGC | TTC | CAC | TGC | CCG | AGC | 384 |
| Ala | Glu | Lys | Leu | Gly | Ile | Pro | Tyr | Phe | Tyr | Gly | Phe | His | Cys | Pro | Ser |  |
|  |  | 115 |  |  |  |  | 120 |  |  |  |  | 125 |  |  |  |  |
| TAT | GTG | CCG | TCG | CCG | TAC | TAT | GCG | CCT | CCG | CCG | CCC | CTC | GGC | GAG | CCG | 432 |
| Tyr | Val | Pro | Ser | Pro | Tyr | Tyr | Ala | Pro | Pro | Pro | Pro | Leu | Gly | Glu | Pro |  |
| 130 |  |  |  |  | 135 |  |  |  |  | 140 |  |  |  |  |  |  |
| CCC | GCA | CCG | GAC | GGG | ACC | GAC | ATC | CAG | GCG | CTG | TGG | GAG | CGC | AAC | AAC | 480 |
| Pro | Ala | Pro | Asp | Gly | Thr | Asp | Ile | Gln | Ala | Leu | Trp | Glu | Arg | Asn | Asn |  |
| 145 |  |  |  |  | 150 |  |  |  |  | 155 |  |  |  |  | 160 |  |
| CAG | AGC | GCC | TAC | CGG | CGG | TAC | GGG | GAG | CCG | CTC | AAC | AGC | AGG | CGC | GCC | 528 |
| Gln | Ser | Ala | Tyr | Arg | Arg | Tyr | Gly | Glu | Pro | Leu | Asn | Ser | Arg | Arg | Ala |  |
|  |  |  |  | 165 |  |  |  |  | 170 |  |  |  |  | 175 |  |  |
| GCC | ATC | GGC | CTG | CCG | CCG | GTG | GAG | GAC | ATC | TTC | GGC | CAC | GGC | TAC | ACC | 576 |
| Ala | Ile | Gly | Leu | Pro | Pro | Val | Glu | Asp | Ile | Phe | Gly | His | Gly | Tyr | Thr |  |
|  |  |  | 180 |  |  |  |  |  | 185 |  |  |  |  | 190 |  |  |
| GAT | CAC | CCG | TGG | ATG | GCG | GCG | GAC | CCG | GTA | CTG | GCC | CCG | CTG | CAA | CCC | 624 |
| Asp | His | Pro | Trp | Met | Ala | Ala | Asp | Pro | Val | Leu | Ala | Pro | Leu | Gln | Pro |  |
|  |  | 195 |  |  |  |  | 200 |  |  |  |  | 205 |  |  |  |  |
| ACG | GAT | CTC | GAC | GCC | GTG | CAG | ACC | GGG | GCG | TGG | ATC | CTG | CCC | GAC | GAA | 672 |
| Thr | Asp | Leu | Asp | Ala | Val | Gln | Thr | Gly | Ala | Trp | Ile | Leu | Pro | Asp | Glu |  |
| 210 |  |  |  |  | 215 |  |  |  |  | 220 |  |  |  |  |  |  |
| CGA | CCG | ATT | TCC | GCT | GAG | CTG | GAG | GCG | TTC | CTG | GAC | GCC | GGC | GCA | CCA | 720 |
| Arg | Pro | Ile | Ser | Ala | Glu | Leu | Glu | Ala | Phe | Leu | Asp | Ala | Gly | Ala | Pro |  |
| 225 |  |  |  |  | 230 |  |  |  |  | 235 |  |  |  |  | 240 |  |
| CCG | GTG | TAC | CTG | GGG | TTC | GGC | AGC | CTT | CGC | GCC | CCC | GCC | GAC | GCC | GCG | 768 |
| Pro | Val | Tyr | Leu | Gly | Phe | Gly | Ser | Leu | Arg | Ala | Pro | Ala | Asp | Ala | Ala |  |
|  |  |  |  | 245 |  |  |  |  | 250 |  |  |  |  | 255 |  |  |
| AAG | GTG | GCC | ATC | GAG | GCG | ATC | CGT | GCC | CAC | GGC | CAC | CGG | GTG | ATC | CTC | 816 |
| Lys | Val | Ala | Ile | Glu | Ala | Ile | Arg | Ala | His | Gly | His | Arg | Val | Ile | Leu |  |
|  |  |  | 260 |  |  |  |  |  | 265 |  |  |  |  | 270 |  |  |
| TCC | CGC | GGC | TGG | GCC | GAT | CTG | GTC | CTG | CCC | GAC | GAC | CGG | GAG | GAC | TGT | 864 |
| Ser | Arg | Gly | Trp | Ala | Asp | Leu | Val | Leu | Pro | Asp | Asp | Arg | Glu | Asp | Cys |  |
|  |  | 275 |  |  |  |  | 280 |  |  |  |  | 285 |  |  |  |  |
| TTC | GCC | ATC | GGC | GAA | GTG | AAT | CAG | CAG | GTG | CTG | TTC | CGC | GGG | GTG | GCC | 912 |
| Phe | Ala | Ile | Gly | Glu | Val | Asn | Gln | Gln | Val | Leu | Phe | Arg | Arg | Val | Ala |  |
|  |  | 290 |  |  |  |  | 295 |  |  |  |  | 300 |  |  |  |  |
| GCC | GTC | ATC | CAC | CAC | GGC | GGC | GCG | GGC | ACG | ACC | CAC | GTG | GCC | ACG | CGG | 960 |
| Ala | Val | Ile | His | His | Gly | Gly | Ala | Gly | Thr | Thr | His | Val | Ala | Thr | Arg |  |
| 305 |  |  |  |  | 310 |  |  |  |  | 315 |  |  |  |  | 320 |  |
| GCG | GGC | GTC | CCC | CAG | ATC | CTG | GTT | CCC | CAG | ATC | GCG | GAC | CAG | CCC | TAC | 1008 |
| Ala | Gly | Val | Pro | Gln | Ile | Leu | Val | Pro | Gln | Ile | Ala | Asp | Gln | Pro | Tyr |  |
|  |  |  |  | 325 |  |  |  |  | 330 |  |  |  |  | 335 |  |  |
| TAC | GCC | GCC | CGG | GTG | GCC | GAA | CTG | GGG | GTC | GGT | GTG | GCG | CAT | GAC | GGC | 1056 |
| Tyr | Ala | Ala | Arg | Val | Ala | Glu | Leu | Gly | Val | Gly | Val | Ala | His | Asp | Gly |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 340 |     |     |     |     | 345 |     |     |     |     |     | 350 |     |      |
| CCG | ACC | CCG | ACC | TTC | GAC | ACG | TTG | TCG | GCG | GCG | CTC | ACC | AAG | GCC | CTC | 1104 |
| Pro | Thr | Pro | Thr | Phe | Asp | Thr | Leu | Ser | Ala | Ala | Leu | Thr | Lys | Ala | Leu |      |
|     |     | 355 |     |     |     | 360 |     |     |     |     | 365 |     |     |     |     |      |
| GCT | CCG | GAA | ACG | CGC | GTG | CGA | GCG | GAA | GCC | GTG | GCG | GAA | ACG | GTC | CAG | 1152 |
| Ala | Pro | Glu | Thr | Arg | Val | Arg | Ala | Glu | Ala | Val | Ala | Glu | Thr | Val | Gln |      |
|     | 370 |     |     |     | 375 |     |     |     |     | 380 |     |     |     |     |     |      |
| ACG | GAC | GGG | GCC | GCG | GTG | GCC | GCG | GAC | CTG | TTG | TTC | GCC | GCG | GTG | ACC | 1200 |
| Thr | Asp | Gly | Ala | Ala | Val | Ala | Ala | Asp | Leu | Leu | Phe | Ala | Ala | Val | Thr |      |
| 385 |     |     |     |     | 390 |     |     |     |     | 395 |     |     |     |     | 400 |      |
| GGG | AAC | CAG | CCC | GCC | GTT | CCC | GCC |     |     |     |     |     |     |     |     | 1224 |
| Gly | Asn | Gln | Pro | Ala | Val | Pro | Ala |     |     |     |     |     |     |     |     |      |
|     |     |     |     | 405 |     |     |     |     |     |     |     |     |     |     |     |      |

( 2 ) INFORMATION FOR SEQ ID NO:2:

( i ) SEQUENCE CHARACTERISTICS:
        ( A ) LENGTH: 408 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Arg | Val | Leu | Leu | Ser | Thr | Cys | Gly | Ser | Arg | Gly | Asp | Val | Glu | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | Val | Ala | Leu | Ala | Val | Arg | Leu | Arg | Glu | Arg | Gly | Ala | Glu | Val | Arg |
|     |     |     |     | 20  |     |     |     |     | 25  |     |     |     |     | 30  |     |
| Met | Cys | Ala | Pro | Pro | Asp | Cys | Ala | Asp | Arg | Leu | Ala | Glu | Val | Asp | Val |
|     |     |     | 35  |     |     |     |     | 40  |     |     |     |     | 45  |     |     |
| Pro | His | Leu | Pro | Leu | Gly | Ala | Ser | Ala | Arg | Pro | Ser | Ala | Gly | Gln | Ala |
|     |     | 50  |     |     |     |     | 55  |     |     |     |     | 60  |     |     |     |
| Lys | Pro | Leu | Thr | Ala | Glu | Asp | Met | Leu | Arg | Phe | Thr | Thr | Glu | Thr | Ile |
| 65  |     |     |     |     | 70  |     |     |     |     | 75  |     |     |     |     | 80  |
| Ala | Thr | Gln | Phe | Glu | Arg | Ile | Pro | Ala | Ala | Ala | Glu | Gly | Cys | Ala | Ala |
|     |     |     |     | 85  |     |     |     |     | 90  |     |     |     |     | 95  |     |
| Val | Val | Thr | Thr | Gly | Leu | Leu | Ala | Ala | Ala | Ile | Gly | Val | Arg | Ser | Val |
|     |     |     | 100 |     |     |     |     | 105 |     |     |     |     | 110 |     |     |
| Ala | Glu | Lys | Leu | Gly | Ile | Pro | Tyr | Phe | Tyr | Gly | Phe | His | Cys | Pro | Ser |
|     |     | 115 |     |     |     |     | 120 |     |     |     |     | 125 |     |     |     |
| Tyr | Val | Pro | Ser | Pro | Tyr | Tyr | Ala | Pro | Pro | Pro | Pro | Leu | Gly | Glu | Pro |
|     | 130 |     |     |     |     | 135 |     |     |     |     | 140 |     |     |     |     |
| Pro | Ala | Pro | Asp | Gly | Thr | Asp | Ile | Gln | Ala | Leu | Trp | Glu | Arg | Asn | Asn |
| 145 |     |     |     |     | 150 |     |     |     |     | 155 |     |     |     |     | 160 |
| Gln | Ser | Ala | Tyr | Arg | Arg | Tyr | Gly | Glu | Pro | Leu | Asn | Ser | Arg | Arg | Ala |
|     |     |     |     | 165 |     |     |     |     | 170 |     |     |     |     | 175 |     |
| Ala | Ile | Gly | Leu | Pro | Pro | Val | Glu | Asp | Ile | Phe | Gly | His | Gly | Tyr | Thr |
|     |     |     | 180 |     |     |     |     | 185 |     |     |     |     | 190 |     |     |
| Asp | His | Pro | Trp | Met | Ala | Ala | Asp | Pro | Val | Leu | Ala | Pro | Leu | Gln | Pro |
|     |     | 195 |     |     |     |     | 200 |     |     |     |     | 205 |     |     |     |
| Thr | Asp | Leu | Asp | Ala | Val | Gln | Thr | Gly | Ala | Trp | Ile | Leu | Pro | Asp | Glu |
|     | 210 |     |     |     |     | 215 |     |     |     |     | 220 |     |     |     |     |
| Arg | Pro | Ile | Ser | Ala | Glu | Leu | Glu | Ala | Phe | Leu | Asp | Ala | Gly | Ala | Pro |
| 225 |     |     |     |     | 230 |     |     |     |     | 235 |     |     |     |     | 240 |
| Pro | Val | Tyr | Leu | Gly | Phe | Gly | Ser | Leu | Arg | Ala | Pro | Ala | Asp | Ala | Ala |
|     |     |     |     | 245 |     |     |     |     | 250 |     |     |     |     | 255 |     |
| Lys | Val | Ala | Ile | Glu | Ala | Ile | Arg | Ala | His | Gly | His | Arg | Val | Ile | Leu |
|     |     |     | 260 |     |     |     |     | 265 |     |     |     |     | 270 |     |     |

Ser Arg Gly Trp Ala Asp Leu Val Leu Pro Asp Asp Arg Glu Asp Cys
    275                 280             Pro         285

Phe Ala Ile Gly Glu Val Asn Gln Gln Val Leu Phe Arg Arg Val Ala
    290             295                 300

Ala Val Ile His His Gly Gly Ala Gly Thr Thr His Val Ala Thr Arg
305                 310                 315                 320

Ala Gly Val Pro Gln Ile Leu Val Pro Gln Ile Ala Asp Gln Pro Tyr
            325                 330                 335

Tyr Ala Ala Arg Val Ala Glu Leu Gly Val Gly Val Ala His Asp Gly
            340                 345                 350

Pro Thr Pro Thr Phe Asp Thr Leu Ser Ala Ala Leu Thr Lys Ala Leu
            355                 360                 365

Ala Pro Glu Thr Arg Val Arg Ala Glu Ala Val Ala Glu Thr Val Gln
    370                 375                 380

Thr Asp Gly Ala Ala Val Ala Ala Asp Leu Leu Phe Ala Ala Val Thr
385                 390                 395                 400

Gly Asn Gln Pro Ala Val Pro Ala
            405

( 2 ) INFORMATION FOR SEQ ID NO:3:

( i ) SEQUENCE CHARACTERISTICS:
        ( A ) LENGTH: 1224 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:3:

```
AUGCGUGUGU UGUUGUCGAC CUGUGGGAGC CGCGGAGACG UCGAACCACU GGUGGCGUUG      60
GCGGUGCGGU UGCGGGAGCG CGGCGCCGAG GUGCGGAUGU GCGCGCCGCC GGACUGCGCG     120
GAUCGGCUGG CCGAAGUCGA CGUGCCGCAU CUGCCCCUCG GUGCGUCGGC GCGCCCGUCG     180
GCCGGGCAGG CGAAACCCUU GACGGCCGAG GACAUGCUCC GGUUCACGAC CGAGACGAUC     240
GCCACGCAGU UCGAGCGGAU UCCGGCGGCC GCCGAAGGAU GCGCCGCGGU GGUGACGACC     300
GGCCUGCUGG CCGCCGCCAU CGGCGUGCGG UCGGUGGCCG AAAAGCUGGG CAUCCCCUAC     360
UUCUAUGGCU UCCACUGCCC GAGCUAUGUG CCGUCGCCGU ACUAUGCGCC UCCGCCGCCC     420
CUCGGCGAGC CGCCCGCACC GGACGGGACC GACAUCCAGG CGCUGUGGGA GCGCAACAAC     480
CAGAGCGCCU ACCGGCGGUA CGGGGAGCCG CUCAACAGCA GGCGCGCCGC CAUCGGCCUG     540
CCGCCGGUGG AGGACAUCUU CGGCCACGGC UACACCGAUC ACCCGUGGAU GGCGGCGGAC     600
CCGGUACUGG CCCCGCUGCA ACCCACGGAU CUCGACGCCG UGCAGACCGG GGCGUGGAUC     660
CUGCCCGACG AACGACCGAU UUCCGCUGAG CUGGAGGCGU CCUGGACGC CGGCGCACCA     720
CCGGUGUACC UGGGGUUCGG CAGCCUUCGC GCCCCGCCG ACGCCGCGAA GGUGGCCAUC     780
GAGGCGAUCC GUGCCCACGG CCACCGGGUG AUCCUCUCCC GCGGCUGGGC CGAUCGGGUC     840
CUGCCCGACG ACCGGGAGGA CUGUUUCGCC AUCGGCGAAG UGAAUCAGCA GGUGCUGUUC     900
CGCCGGGUGG CCGCCGUCAU CCACCACGGC GGCGCGGGCA CGACCCACGU GGCCACGCGG     960
GCGGGCGUCC CCCAGAUCCU GGUUCCCCAG AUCGCGGACC AGCCCUACUA CGCCGCCCGG    1020
GUGGCCGAAC UGGGGGUCGG UGUGGCGCAU GACGGCCCGA CCCCGACCUU CGACACGUUG    1080
```

| | | | | | | |
|---|---|---|---|---|---|---|
| UCGGCGGCGC | UCACCAAGGC | CCUCGCUCCG | GAAACGCGCG | UGCGAGCGGA | AGCCGUGGCG | 1140 |
| GAAACGGUCC | AGACGGACGG | GGCCGCGGUG | GCCGCGGACC | UGUUGUUCGC | CGCGGUGACC | 1200 |
| GGGAACCAGC | CCGCCGUUCC | CGCC | | | | 1224 |

GLUCOSYLTRANSFERASE GENE GTFE FROM AMYCOLATOPSIS ORIENTALIS

This application claims benefit of priority of U.S. Provisional Application No. 60/026,055, filed on Sep. 13, 1996.

BACKGROUND OF THE INVENTION

This invention relates to recombinant DNA technology. In particular the invention pertains to the cloning of a glycosyltransferase gene from *Aiycolatopsis orientalis,* the use of the cloned gene to express and purify the encoded enzyme, and a method of using the cloned enzyme in the production of glycopeptide compounds.

The use of antibiotic compounds has had a profound impact on the practice of medicine in the United States and around the world. Two highly effective antibiotic compounds of the glycopeptide class, vancomycin and teichoplanin, have been approved for use in humans.

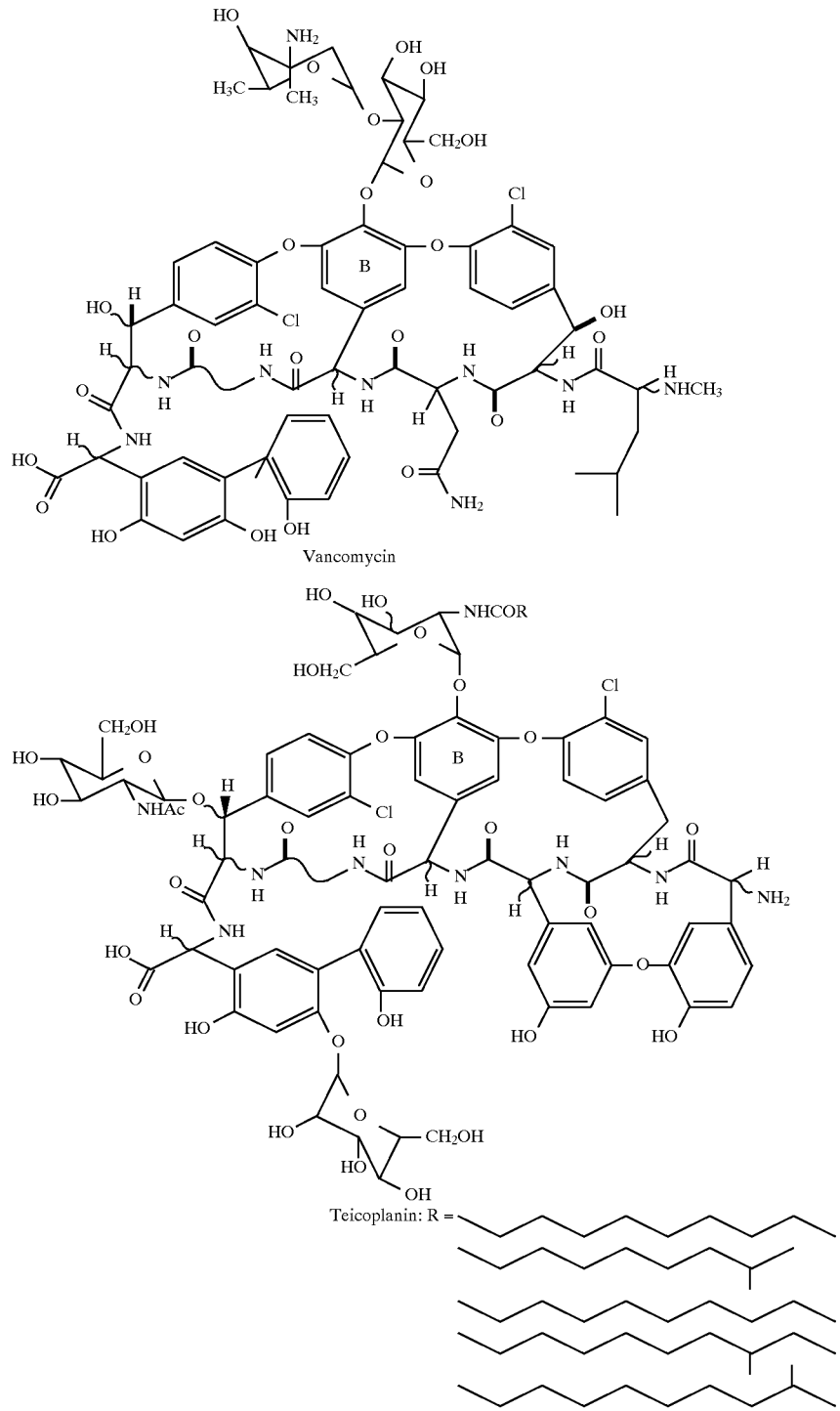

The glycopeptide antibiotics comprise natural and semi-synthetic compounds of highly functionalized linear heptapeptides having a core structure composed of either seven modified or unusual aromatic amino acids, or a mix of aromatic and aliphatic amino acids. Natural glycopeptide compounds have been found in a variety of bacterial genera including Streptomyces, Actinoplanes, Nocardia, Amycolatopsis, Kibdelosporangia, and Pseudonocardia. M. Zmijewski and J. Fayerman. "Glycopeptide Antibiotics," In *Genetics and Biochemistry of Antibiotic Production,* Chap. 18. Ed. L. C. Vining and C. Studtard. Publ. Butterworth Heinemann, Boston (1995). Generally, glycopeptide compounds are differentiated by the placement of sugar substituents on the peptide core. In some instances differentiation arises from the positioning of fatty acid moieties on said sugar substituents. Research has shown that the sugar moieties attached to the core may have an effect on the biological activity of glycopeptide molecules.

At present, investigations into glycosylation of glycopeptides and glycopeptide cores are limited to preliminary observations on crude cellular extracts of bacterial strains that produce glycopeptide compounds. These experiments have demonstrated that the glycosylation reaction appears to involve one or more enzymatic activities which attach sugar residues onto a glycopeptide core. One study, for example, demonstrated a glycosylating activity in a crude cellular extract of a vancomycin-producing strain of *Amycolatopsis orientalis*. M. Zmijewski & B. Briggs. "Biosynthesis of vancomycin: identification of TDP-glucose:aglycosylvancomycin glucosyltransferase from *Amycolatopsis orientalis*" FEMS Microbiol. Lett. 59, 129–134 (1989).

The glycosylation of glycopeptide compounds, intrinsically interesting from a scientific point of view, presents a number of practical considerations that warrant continued study of this subject. Recently, a number of glycopeptide resistant strains of pathogenic organisms have been encountered within the clinical environment. This trend toward diminished efficacy of glycopeptide compounds is alarming because of a similar phenomenon in the case of β-lactam antibiotics. It is clear that the rise in antibiotic resistance has occurred by a plurality of molecular mechanisms and that resistant organisms possess a diverse repertoire for counteracting the otherwise lethal effect of antibiotic compounds.

In light of the trend toward greater resistance, and in view of the absence of effective alternative treatments, there exists a pressing need to develop new antibiotic compounds. A useful strategy toward this end involves derivitizing presently available glycopeptide compounds by engineering in defined ways the placement and configuration of sugar moieties on the glycopeptide core structure. Achieving molecular rearrangements and substitutions of sugars on glycopeptide compounds by chemical means is difficult if not impossible in most cases. By contrast to chemical procedures, enzymatic methods, if available, would provide an effective means to engineer specific modifications onto the glycopeptide core.

The challenge to provide an enzymatic means for modifying glycopeptides or glycopeptide core molecules has been met by the present invention. Described herein are gtfE genes isolated from *Amycolatopsis orientalis* which encode glycosyltransferase enzyme GtfE, which adds D-glucose or D-xylose moieties onto the B ring of vancomycin and teichoplanin glyopeptides and core molecules.

BRIEF SUMMARY

The present invention is designed to meet the aforementioned need and provides, inter alia, the isolated gtfE gene and other nucleic acid molecules that encode the GtfE gene product from *Amycolatopsis orientalis* C329.4. The invention also provides the GtfE protein product of the *Amycolatopsis orientalis* gtfE gene, in substantially purified form. Both the native *Amycolatopsis orientalis* gene gtfE, which encodes the activity, as well as a PCR-derived variant thereof, are used to produce proteins which exhibit this activity in a recombinant host cell. The GtfE proteins produced by recombinant methods are useful in the production of novel glycopeptide compounds.

Having the cloned gtfE gene of *Amycolatopsis orientalis* enables the production of recombinant GtfE protein from which can be made novel derivatives of glycopeptide compounds.

In one embodiment the present invention relates to an isolated DNA molecule encoding GtfE protein, said DNA molecule comprising the nucleotide sequence identified as SEQ ID NO. 1:
ATGCGTGTGT TGTTGTCGAC CTGTGGGAGC CGCG-GAGACG TCGAACCACT GGTGGCGTTG 60 GCGGT-GCGGT TGCGGGAGCG CGGCGCCGAG GTGCG-GATGT GCGCGCCGCC GGACTGCGCG 120
GATCGGCTGG CCGAAGTCGA CGTGCCGCAT CTGC-CCCTCG GTGCGTCGGC GCGCCCGTCG 180
GCCGGGCAGG CGAAACCCTT GACGGCCGAG GACATGCTCC GGTTCACGAC CGAGACGATC 240
GCCACGCAGT TCGAGCGGAT TCCGGCGGCC GCCGAAGGAT GCGCCGCGGT GGTGACGACC 300
GGCCTGCTGG CCGCCGCCAT CGGCGTGCGG TCG-GTGGCCG AAAAGCTGGG CATCCCCTAC 360 TTC-TATGGCT TCCACTGCCC GAGCTATGTG CCGTCGC-CGT ACTATGCGCC TCCGCCGCCC 420
CTCGGCGAGC CGCCCGCACC GGACGGGACC GACATCCAGG CGCTGTGGGA GCGCAACAAC 480
CAGAGCGCCT ACCGGCGGTA CGGGGAGCCG CTCAACAGCA GGCGCGCCGC CATCGGCCTG 540
CCGCCGGTGG AGGACATCTT CGGCCACGGC TACACCGATC ACCCGTGGAT GGCGGCGGAC 600
CCGGTACTGG CCCCGCTGCA ACCCACGGAT CTC-GACGCCG TGCAGACCGG GGCGTGGATC 660 CTGC-CCGACG AACGACCGAT TTCCGCTGAG CTGGAG-GCGT TCCTGGACGC CGGCGCACCA 720
CCGGTGTACC TGGGGTTCGG CAGCCTTCGC GCCCCCGCCG ACGCCGCGAA GGTGGCCATC 780
GAGGCGATCC GTGCCCACGG CCACCGGGTG ATC-CTCTCCC GCGGCTGGGC CGATCTGGTC 840 CTGC-CCGACG ACCGGGAGGA CTGTTTCGCC ATCGGC-GAAG TGAATCAGCA GGTGCTGTTC 900
CGCCGGGTGG CCGCCGTCAT CCACCACGGC GGCGCGGGCA CGACCCACGT GGCCACGCGG 960
GCGGGCGTCC CCCAGATCCT GGTTCCCCAG ATCGCGGACC AGCCCTACTA CGCCGCCCGG 1020
GTGGCCGAAC TGGGGGTCGG TGTGGCGCAT GACGGCCCGA CCCCGACCTT CGACACGTTG 1080
TCGGCGGCGC TCACCAAGGC CCTCGCTCCG GAAACGCGCG TGCGAGCGGA AGCCGTGGCG 1140
GAAACGGTCC AGACGGACGG GGCCGCGGTG GCCGCGGACC TGTTGTTCGC CGCGGTGACC 1200
GGGAACCAGC CCGCCGTTCC CGCC 1224

In another embodiment the present invention relates to a Glycosyltransferase protein molecule, encoded by SEQ ID NO:1 wherein said Glycosyltransferase protein molecule comprises the sequence identified as SEQ ID NO. 2.

In a further embodiment the present invention relates to a ribonucleic acid molecule encoding GtfE protein, said ribonucleic acid molecule comprising the sequence identified as SEQ ID NO. 3:

In yet another embodiment, the present invention relates to a recombinant DNA vector which incorporates the *Amrycolatopsis orientalis* gtfE gene in operable linkage to gene expression sequences enabling the gtfE gene to be transcribed and translated in a host cell.

In still another embodiment the present invention relates to homologous or heterologous host cells which have been transformed or transfected with the cloned gtfE gene of *Amiycolatopsis orientalis* such that the gtfE gene is expressed in the host cell.

In still another embodiment, the present invention relates to a method for producing glycopeptide compounds wherein GtfE protein produced by recombinant cells is utilized to add one or more sugar moieties onto a glycopeptide or glycopeptide core, in vitro or in vivo.

In yet another embodiment, the present invention relates to novel glycopeptide compounds.

DEFINITIONS

Figure 1:
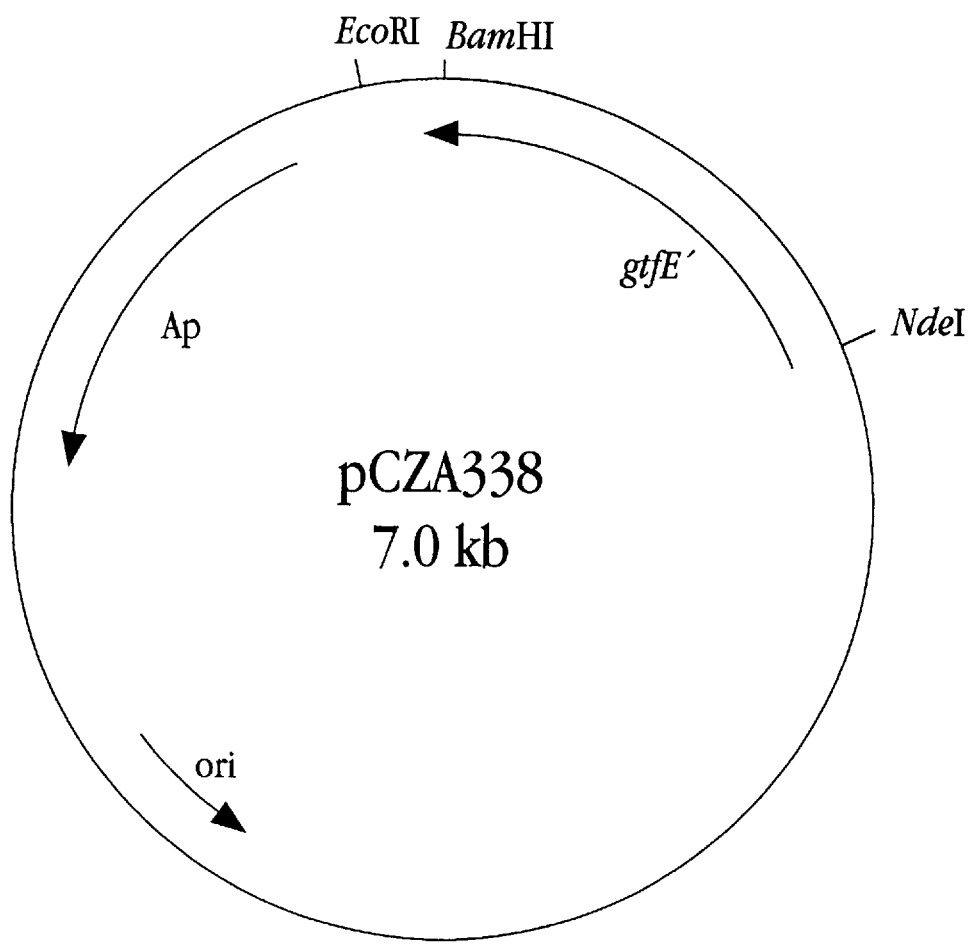
FIG. 1. Plasmid pCZA338, which is useful for high level expression of the *Amycolatopsis orientalis* GtfEp enzyme activity in heterologous or homologous procaryotic host cells.
Figure 2:
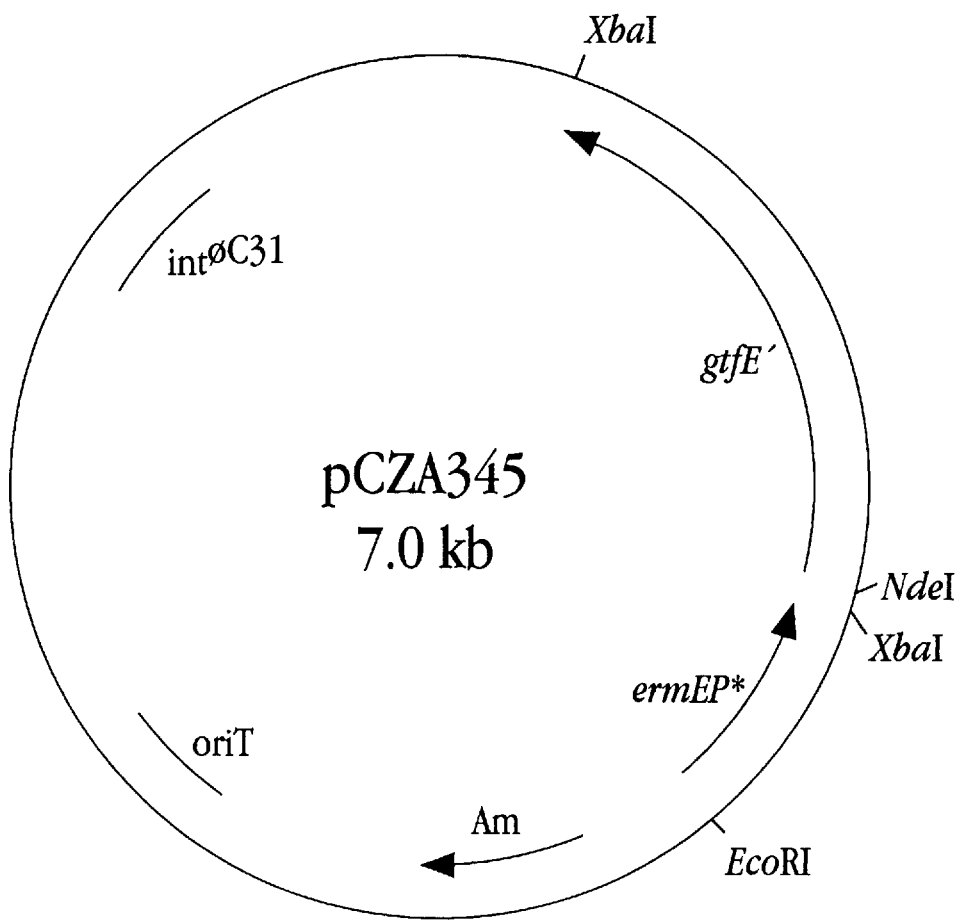
FIG. 2. Plasmid pCZA345, which may be used to express the *Amycolatopsis orientalis* GtfEp enzyme activity in heterologous host *Streptonyces toyocaensis*.

"AGV," which denotes aglycosylvancomycin, comprises a vancomycin core having a free hydroxl group on the B ring in place of the disaccharide moiety.

"A47934" and "A41030A" refer to glycopeptide compounds, comprising a teichoplanin core, and naturally lacking a sugar moiety. A47934 is produced in *Streptomyces toyocaensis*; A41030A is produced in *Streptomyces virginiae*.

"gtfE" refers to the native genomic sequence which encodes glucosyltransferase enzyme activity in *Amycolatopsis orientalis*. This sequence is identified as SEQ ID NO.1.

"gtfEp" refers to a PCR-derived variant of gtfE having two base pair changes in SEQ ID NO.1, at position 1003, where a "T" residue is inserted in place of a "C" residue, and at position 1179 where a "T" residue is inserted in place of a "C" residue. This variant was produced during a PCR reaction. It also encodes an active glucosyltransferase enzyme activity.

"GtfE" refers to the glucosyltransferase encoded by gtfE and identified as SEQ ID NO.2.

"GtfEp" refers to the glucosyltransferase encoded by gtfep, the PCR variant, wherein a single amino acid substitution occurs in SEQ ID NO.2, at position 335, where Ser replaces Pro. GtfE and GtfEp exhibit glucosyltransferase enzyme activity.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Exconjugant" refers to Actinomycetes or other cell type which has incorporated a cloning vector, or other DNA, or recombinant DNA molecule following conjugal transfer from *E. coli*.

The term "glycopeptide" refers to a functionalized linear heptapeptide compound of natural or semi-synthetic origin, said compound having a core structure.

"Glycopeptide core" or "core" or "core compound" interchangeably denote the progenitor structure of all glycopeptide compounds, comprising either 7 modified or unusual aromatic amino acids or a mix or aromatic and aliphatic amino acids.

"Glycosylating substrate" refers to a compound which functions as a donor of a sugar moiety in an enzymatic glycosylation reaction, for example, uridine diphosphate-D-glucose.

"Glucosyltransferase" means GtfE or GtfEp, or functional equivalent thereof.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which two or more strands of nucleic acid join through base pairing with complementary strands. "Selective hybridization" refers to hybridization under conditions of high stringency. The degree of hybridization between nucleic acid molecules varies with the degree of complementarity, the stringency of the hybridization conditions, and the length of the strands.

The term "stringency" refers to a set of hybridization conditions, for example temperature and salt concentration, which may be varied to achieve "high stringency" or "low stringency" conditions, thereby varying the degree of hybridization of one nucleic acid molecule with another nucleic acid molecule. High stringency conditions disfavor non-homologous basepairing.

DETAILED DESCRIPTION

The gtfE gene of *Amycolatopsis orientalis* encodes a glycosylating enzyme, GtfE. The enzyme will add D-glucose or D-xylose onto the free hydroxl group of the B ring of aglycosylvancomycin (AGV), producing desvancosaminylvancomycin (DVV), or the xylose derivative thereof. The enzyme uses TDP-glucose, UDP-glucose, or UDP-xylose as the glycosylating substrate. The cloned GtfE enzyme will also add D-glucose onto teichoplanin cores such as A47934 and A41030. (see Table).

TABLE

| Glycosylating Substrate | Glycopeptide | | |
|---|---|---|---|
| | AGV | A41036 | A47934 |
| No sugar | − | − | − |
| TDP-glucose | + | + | + |
| UDP-glucose | + | + | + |
| UDP-galactose | − | | |
| UDP-mannose | − | | |
| UDP-xylose | + | | |
| UDP-N-acetylglucosamine | − | | |
| UDP-galactouronic acid | − | | |

The gtfE gene of *Amycolatopsis orientalis* comprises a DNA sequence of 1224 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product identified as SEQ ID NO:2. All such substitutions are intended to be within the scope of the invention. Moreover, skilled artisans will recognize that many amino acid substitutions may be made without altering the activity or function of a protein. All such substitutions are intended to be within the scope of this invention. For example, one specific variant of gtfE was isolated during a PCR. This variant, termed gtfEp, introduces two base pair changes in SEQ ID NO.1 resulting in one amino acid change in SEQ ID NO.2 (See Definitions). The gtfep variant and the protein it encodes, GtfEp, encode a functional glucosyltransferase activity.

Gene Isolation Procedures

Those skilled in the art will recognize that the GtfE gene may be obtained by a plurality of applicable techniques including, for example, polymerase chain reaction (PCR) amplification, or de novo DNA synthesis. (See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J.Sambrook et al. Supra]. Suitable cloning vectors are widely available.

Skilled artisans will recognize that the gtfE gene of *Amrycolatopsis orientalis* or fragment thereof could also be isolated by PCR amplification of *Amiycolatopsis orientalis* genomic DNA using oligonucleotide primers targeted to any suitable region of SEQ ID NO. 1. Methods for PCR amplification are widely known in the art. See e.g. *PCR Protocols: A Guide to Method and Application,* Ed. M. Innis et al., Academic Press (1990), which hereby is incorporated by reference. The PCR amplification, which comprises genomic DNA, suitable enzymes, primers, and buffers, is conveniently carried out in a DNA Thermal Cycler (Perkin Elmer Cetus, Norwalk, Conn.). A positive PCR amplification is determined by detecting an appropriately-sized DNA fragment following agarose gel electrophoresis.

The gtfE gene, which comprises nucleic acid encoding SEQ ID NO:2, may also be produced using synthetic methodology. The synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the gtfE gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach,* (1984).]

The ribonucleic acids of the present invention may be prepared using the polynucleotide synthetic methods discussed supra, or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. These RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for a variety of molecular biology techniques. For example, the nucleic acid compounds of the present invention may be used to hybridize to genomic DNA which has been digested with one or more restriction enzymes and separated on an electrophoretic gel. The hybridization of radiolabeled probes onto such restricted DNA, usually fixed to a membrane after electrophoresis, is well known in the art. See, e.g., J. Sambrook, supra. A compound which comprises SEQ ID NO:1, SEQ ID NO:3 or a complementary sequence of SEQ ID NO:1 or SEQ ID NO:3, or a fragment thereof, and which is at least 18 base pairs in length, and which will selectively hybridize to *Amycolatopsis orientalis* DNA or mRNA encoding gtfE, is provided. Preferably, the 15 or more base pair compound is DNA. The probes and primers of this invention can be prepared by techniques well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO:1.

Choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers and metabolic markers), and the desired number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. A number of inducible promoters responding to a variety of induction signals are available, for example, carbon source, metal ions, and heat. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli* which has been transfected or transformed with a vector which comprises a nucleic acid of the present invention. Another preferred host is *Streptomyces toyocaensis*.

The present invention also provides a method for constructing a recombinant host cell capable of expressing SEQ ID NO:2, said method comprising transforming or otherwise introducing into a host cell a recombinant DNA vector that comprises an isolated DNA sequence which encodes SEQ ID NO:2. A preferred host cell is any strain of *E. coli* which can accomodate high level expression of a gene(s) introduced by transformation or transfection. Preferred vectors for expression are those which comprise SEQ ID NO:1. Transformed host cells may be cultured under conditions well known to skilled artisans such that SEQ ID NO:2 is expressed, thereby producing GtfE protein in the recombinant host cell.

Protein Production Methods

One embodiment of the present invention relates to the substantially purified protein GtfE identified as SEQ ID NO:2 and encoded by the gtfE gene or functionally related proteins of *Amycolatopsis orientalis*.

Skilled artisans will recognize that the proteins of the present invention can be synthesized or purified by any number of suitable methods. For example, the amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and are described in a number of general texts on the subject. See, e.g., H. Dugas and C. Penney, *Bioorganic Chemistry* (1981) Springer-Verlag, New York, 54–92. For example, peptides may be synthesized by solid-phase methodology using an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably −20_C. for thirty minutes followed by thirty minutes at 0_C.

The proteins of the present invention can also be produced by recombinant DNA methods using the cloned gtfE gene of *Amycolatopsis orientalis*. Recombinant methods are preferred if a high yield is desired. Expression of the cloned gtfE gene can be carried out in a variety of suitable host cells well known to those skilled in the art. The gtfE gene is introduced into a host cell by any suitable transformation, transfection, or conjugation means, well known to those skilled in the art. While chromosomal integration of the cloned gtfE gene is within the scope of the present invention, it is preferred that the gene be cloned into a suitable extra-chromosomally maintained expression vector in which the coding region of the gtfE gene is operably linked to a constitutive or inducible promoter.

The basic steps in the recombinant production of the GtfE protein are:

a) constructing a natural, synthetic or semi-synthetic DNA encoding GtfE protein;

b) integrating said DNA into an expression vector in a manner suitable for expressing the GtfE protein, either alone or as a fusion protein;

c) transforming, transfecting, or otherwise introducting said expression vector into an appropriate eukaryotic or prokaryotic host cell to form a recombinant host cell, d) culturing said recombinant host cell under conditions that favor expression of the GtfE protein; and e) recovering and purifying the GtfE protein by any suitable means.

Expressing Recombinant GtfE Protein in Procaryotic and Eucaryotic Host Cells

In general, prokaryotes are used for cloning DNA and for constructing the vectors of the present invention. Prokaryotes are also employed in the production of the GtfE protein. For example, the *Escherichia coli* K12 strain 294 (ATCC No. 31446) is particularly useful for the expression of foreign proteins. Other strains of E. coli, bacilli such as Bacillus subtilis, enterobacteriaceae such as Salmonella typhimurium or Serratia marcescans, various Pseudomonas species, and other bacteria, such as Streptomyces, may also be employed as host cells in the cloning and expression of the recombinant proteins of this invention.

Promoters suitable for driving the expression of gene sequences in prokaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATHI (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized by recombinant or chemical means as the amino acid sequence identified as SEQ ID NO:2, or as a fusion protein comprising the protein of interest and another protein or peptide which may be removable by enzymatic or chemical cleavage. Expression as a fusion protein may prolong the lifespan, increase the yield of the desired peptide, or provide a convenient means for purifying the protein. A variety of peptidases (e.g. enterokinase and thrombin) which cleave a polypeptide at specific sites are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in Protein Purification: From Molecular Mechanisms to Larae Scale Processes, American Chemical Society, Washington, D.C. (1990).

In addition to prokaryotes, mammalian host cells and eukaryotic microbes such as yeast may also be used to isolate and express the genes of the present invention. The simple eucaryote Saccharomyces cerevisiae, is the most commonly used eukaryotic microorganism, although a number of other yeasts such as Kluyveromyces lactis are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRPI gene which provides a selectable marker for use in a trpl auxotrophic mutant.

Purification of GtfE Protein Produced in Recombinant Host

The recombinantly produced protein may be purified from cellular extracts of transformed cells by any suitable means. In a preferred protein purification method, the gtfE gene is modified at the 5' end to incorporate several histidine residues at the amino terminus of the GtfE protein product. The "histidine tag" enables a single-step protein purification method referred to as "immobilized metal ion affinity chromatography" (IMAC), essentially as described in M. C. Smith et al. "Chelating Peptide-immobilized metal-ion affinity chromatography," Chapter 12, in Protein Purification: From Molecular Mechanisms to Large Scale Processes, American Chemical Society, Washington, D.C. (1990), and in U.S. Pat. No. 4,569,794 both of which hereby are incorporated by reference. The IMAC method enables rapid isolation of substantially pure protein.

Synthesis of Glycope-tide Compounds Using a Cloned Enzyme

The cloned GtfE enzyme is useful for developing new glycopeptide compounds by, for example, glycosylating already existing glycopeptide compounds and cores in vivo or in vitro. A method embodied herein comprises glycosylating a glycopeptide or glycopeptide core compound, by contacting the glycopeptide with the cloned GtfE protein and monitoring the glycopeptide compound that is produced.

The instant invention provides an enzymatic method for glycosylating vancomycin and teichoplanin core compounds using the cloned A. orientalis gtfE gene, said method comprising the steps of:
  a) expressing the cloned gtfE gene in a host cell so that GtfE enzyme is produced;
  b) exposing said GtfE enzyme to a glycopeptide or core compound, in viva or in vitro;
  c) providing a suitable glycosylating substrate; and
  d) characterizing and/or purifying the product glycopeptide by any suitable means.

An expression vector carrying the cloned gtfE gene of Amycolatopsis orientalis is transformed, transfected, or introduced by conjugation into a suitable host cell using standard methods. Suitable conjugation methods are described in P. Matsushima and R. H. Baltz, "A gene cloning system for Streptomyces toyocaensis" Microbiol. 142, 261–267 (1996), which hereby is incorporated by reference. Cells which contain the vector are propagated under conditions suitable for expression of the Glycosyltransferase protein. If the gtfE gene is under the control of an inducible promoter, growth media and other conditions should incorporate the appropriate inducer.

The instant method can be used to enzymatically attach sugar residues to glycopeptide or glycopeptide cores such as, for example, members of the vancomycin and teichoplanin core structures. The method will, for example, attach a D-glucose or D-xylose moiety at the free hydroxyl group of the B ring of aglycosylvancomycin. The method can also be used to glucosylate teichoplanin cores that naturally lack sugar residues, such as, for example, compounds A41030A and A47934 (See e.g. M. Zmijewski and J. Fayerman. "Glycopeptide Antibiotics," In Genetics and Biochemistry of Antibiotic Production, Chap. 18. Ed. L. C. Vining and C. Studtard. Publ. Butterworth Heinemann, Boston (1995)).

The method can be adapted to substantially purified recombinant GtfE protein, as described herein, or to a crude cellular extract isolated from a recombinant cell culture that expresses the GtfE protein by virtue of having been transformed, transfected, or conjugated with the Amycolatopsis orientalis gtfE gene.

The invention also comprises in vivo glycosylation reactions in which the cloned A. orientalis gtfe gene is introduced into a glycopeptide-producing bacterial strain such that under suitable growth conditions the glycopeptide compound, which is indigenous to the strain, is specifically glycosylated intracellularly. For example, the gtfE gene may be introduced into an A47934-producing strain of *S. toyocaensis* such that compound A47934, which naturally lacks a sugar moiety, is glucosylated at the free hydroxl group of the B ring. The preferred method for introducing the gtfE gene into *S. toyocaensis* is by conjugation with an *E. coli* strain which carries the gtfE gene on a suitable recombinant plasmid.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector Containing the gtfE Gene

A gtfE gene cassette may be conveniently generated from *A. orientalis* genomic DNA by PCR. Suitable oligonucleotide primers are synthesized to contain appropriate cloning sites and regions complementary to the terminal region of SEQ ID NO.1. The amplified DNA which comprises the gtfE gene cassette is then ligated into any suitable vector, for example, pET11A (Novogen, Madison, Wis.).

EXAMPLE 2

Construction of a DNA Vector Containing gtfEp Gene

A gtfEp gene cassette may be conveniently made by any suitable site-directed mutagenesis procedure. A suitable commercially available kit, "MORPH," utilizes a DpnI hemimethylation procedure (available from 5 Prime 3 Prime, Inc. Boulder, Colo. 80303).

Briefly, a plasmid carrying the wild-type sequence, gtfE, is prepared from any dam$^+$ *E.coli*, such as DH5α, HB101, RR1, and JM101. The purified target DNA is then denatured at 100_C. and annealed to an oligonucleotide which carries the desired mutation. In this case, a "T" is inserted in place of a "C" at position 1003 of SEQ ID NO.1. The oligonucleotide is extended with T4 DNA polymerase to generate hemi-methylated, double-stranded DNA molecules resistant to digestion by DpnI endonuclease. Following transformation into a mutS bacterial strain colonies which carry the mutated gene may be identified by any suitable means well known to those skilled in the art. A second round of mutagenesis can be carried out in order to introduce a "T" in place of a "C" at position 1179 of SEQ ID NO.1. The desired cassette can then be inserted into a suitable vector by any suitable means.

EXAMPLE 3

Construction of a DNA Vector which expresses in *Escherichia coli* a glycosylase activity encoded by a glucosyltranserase gene of *Amycolatopsis orientalis*

Plasmid pCZA338 (see FIG. 1) is an approximately 7 kilobasepair expression vector suitable for expressing the gtfEp gene at high levels in a procaryotic host, for example *E. coli*. Plasmid pCZA338 was derived from parent plasmid PET-11a (obtained from Novagen, Madison, Wis.), which contains an origin of DNA replication (ori), an ampicillin resistance gene (Amp), the T7 promoter region, and the lacI gene for repressing the lac operon.

The gtfEp gene cassette inserted into pCZA338 was generated by the PCR carried out on genomic DNA isolated from *A. orientalis* strain C329.4 (NRRL accession # 2452) using standard conditions. Primers used in the amplification reaction were complementary to the 5' and 3' ends of the gtfE gene sequence specified in SEQ ID NO: 1 and were engineered to contain NdeI and BglII restriction sites. The PCR-amplified gtfEp gene sequence was digested with NdeI and BglII and ligated into pETlla, which had been digested with NdeI and BamHI.

The gtfEp gene cassette in pCZA338 encodes a single amino acid substitution in SEQ ID NO.2 wherein a Pro at position 335 is replaced by a Ser at position 335. The protein encoded by gtfEp, designated GtfEp, retains glycosyltransferase enzyme activity.

EXAMPLE 4

Construction of a Vector for Expressing the *Amycolatopsis orientalis* glycosyltransferase activity in *Streptomyces toyocaensis*

Plasmid pCZA338 (see Example 3) was digested with XbaI and HindIII and an approximately 1.5 Kb DNA fragment carrying the gene was isolated by agarose gel electrophoresis and ligated into XbaI and HindIII-digested pIJ4070. pIJ4070 is a derivative of pIJ2926 [Jannsen, G. et al. Gene 124, 133 (1993)] in which the ermEp promoter (functional in *S. toyocaensis*), carried on a KpnI to BalmHI fragment, has a 3 bp deletion in the −35 region [Schmitt-John and Engels, Appl. Microbiol. Biotechnol. 36, 493 (1992)]. The plasmid resulting from the ligation of said gene cassette and pIJ4070, designated pCZA340, was digested with BglII and an approximately 1.8 Kb fragment which contained the ermEp promoter and the gene sequence encoding glycosyltransferase activity, was ligated into appropriately restricted pSET152 [Bierman, M. et al. Gene, 116, 43 (1992)]. The resulting plasmid, pCZA345, is approximately 7 kilobase pair and will transform *E. coli* efficiently. Plasmid pCZA345 also enables expression of *A. orientalis* glycosyltransferase activity in *S. toyocaensis* following conjugation with an *E. coli* cell harboring plasmid pCZA345.

EXAMPLE 5

Transformation of *Escherichia coli* with an Expression Plasmid which encodes a glycosyltransferase activity derived from *Amycolatopsis orientalis*

Plasmid pCZA338 was transformed into *E. coli* BL21 (DE3)(hsdS gal λcIts857 indlSam7nin51acUV5-T7gene 1) using standard methods (See e.g. Sambrook et al. Supra).

EXAMPLE 6

Introduction of Plasmid pCZA345 into *S. toyocaensis* by Conjugation

Plasmid pCZA345 was tranformed by standard methods into *E. coli* strain S17-1. For conjugation from *E. coli* to *Streptomyces toyocaensis* about 100 µl of a spore stock comprising *S. toyocaensis* A80934 (~4×10$^8$/ml) was mixed with 50 µl stationary phase S17-1 containing pCZA345 and spread onto the surface of modified R2 agar. The agar plates were incubated for 16–24 hours at 29° C., then apramycin plus naladixic acid in 3 ml soft nutrient agar was added to the surface of each plate to give a final bottom agar concentration of 25 µg/ml for each antibiotic. The plates were incubated for 5 to 10 days and apramycin resistant exconjugants were counted.

EXAMPLE 7

In Vitro Glycosylation of Desyancosaminyl Vancomycin Using Cloned Gene from *Amycolatopsis orientalis*

Approximately 25 ml of a culture of *E. coli* BL21(DE3) cells transformed with plasmid pCZA338 were grown to an $OD_{600}$ of about 0.6. Induction of gene expression was effected by adding 1 mM IPTG with shaking at room temperature for 2 to 3 hours. Thereafter, cells from about 20 ml of the induced culture were pelleted by centrifugation and resuspended in 2 ml of 50 mM Tris pH 9.0, 100 μg/ml lysozyme with incubation on ice for 10 minutes to effect cell lysis. After cell lysis the suspension was passed through a 23-gauge syringe and centrifuged at 10,000×g for 15 minutes to pellet cell debris. The resulting cell extract was used for the glycosylation reaction.

The 1 ml glycosylation reaction contained:

1 mg AGV in 50 mM Tris HCl, pH 9.0

5 mg TDP-glucose 1 mg bovine serum albumin (BSA)

20 μl 1M $MgCl_2$

20 μl 1M $CaCl_2$

5 μl 1M dithiothreitol (DTT)

445 μl cell extract

Distilled water to 1 ml.

A control reaction contained cell extract from non-transformed BL21(DE3). After incubation overnight at 37_C. with slight shaking the reaction was filtered through a 0.45 micron filter and analyzed by HPLC. The test sample but not the control showed a new peak appearing at about 10 minutes retention time. The new peak was found by mass spectrometry to possess the mass expected of desyancosaminyl vancomycin. (Data not shown).

EXAMPLE 8

In Vivo Glycosylation of a Glycopeptide in *Streptomyces toyocaensis* Using Cloned *Amycolatopsis orientalis* Glycosyltransferase Gene Recombinant *S. toyocaensis* A80934 carrying plasmid pCZA345 (prepared as described in Example 6) was fermented on a glucose containing medium for 7 days at $30_{13}$ C. The fermentation medium contained (per liter): glucose—15 g; potato dextrin—30 g; blackstrap molasses—3 g; nutrisoy flour—15 g; casein—5 g; $CaCO_3$—5 g, at pH 6.8–7.0. After fermentation the cells were extracted and the glycopeptide constituents analyzed by HPLC, as described in Zmijewski et al. Antimicrob. Agents. Chemother. 31, 1497–1501 (1987). The HPLC analysis revealed a new peak which was absent in the untransformed control.

EXAMPLE 9

Bioactivity of a Glycosylated A47934 Produced In Vivo in *Streptococcus toyocaensis*

The glycosylated A47934 produced in Example 8 was purified by preparative HPLC methodology from crude cellular extracts of exconjugants using a Waters C18 Nova-Pak column (40×300 mm) and UV detection at 280 nm. Elution was accomplished with a linear gradient of 5% CH3CN— 95% buffer to 80% CH3CN—20% buffer over 30 minutes. The buffer used was 0.5% triethylamine in water, adjusted to pH 3 with H3PO4. The desired fractions were subsequently desalted with a Waters C18 Sep-Pak (35 cc) and lyophilized.

The HPLC-purified glycosylated A47934 was demonstrated to have antibacterial activity when tested by a standard plate assay.

---

We claim:

1. An isolated nucleic acid compound comprising a sequence encoding the protein having the amino acid sequence which is SEQ ID NO 2.

2. An isolated nucleic acid compound comprising a protein wherein at amino acid position 335 of SEQ ID NO:2 Ser is substituted for Pro.

3. An isolated nucleic acid compound comprising a sequence encoding the protein of SEQ ID NO.2 wherein said compound has a sequence selected from the group consisting of:

(a) ATGCGTGTGT TGTTGTCGAC CTGTGGGAGC CGCGAGACG TCGAACCACT GGTGGCGTTG 60
GCGGTGCGGT TGCGGGAGCG CGGCGCCGAG GTGCGGATGT GCGCGCCGCC GGACTGCGCG 120
GATCGGCTGG CCGAAGTCGA CGTGCCG- CAT CTGCCCCTCG GTGCGTCGGC GCGC- CCGTCG 180 GCCGGGCAGG CGAAACCCTT GACGGCCGAG GACATGCTCC GGTTCACGAC CGAGACGATC 240
GCCACGCAGT TCGAGCG- GAT TCCGGCGGCC GCCGAAGGAT GCGC- CGCGGT GGTGACGACC 300 GGCCTGCTGG CCGCCGCCAT CGGCGTGCGG TCGGTGGCCG AAAAGCTGGG CATCCCCTAC 360
TTCTATGGCT TCCACTGCCC GAGCTATGTG CCGTCGCCGT ACTATGCGCC TCCGCCGCCC 420 CTCGGC- GAGC CGCCCGCACC GGACGGGACC GACATC- CAGG CGCTGTGGGA GCGCAACAAC 480 CAG- CAGCGCCT ACCGGCGGTA CGGGGAGCCG CTCAACAGCA GGCGCGCCGC CATCGGCCTG 540
CCGCCGGTGG AGGCATCTT CGGCCACGGC TACACCGATC ACCCGTGGAT GGCGGCGGAC 600
CCGGTACTGG CCCCGCTGCA ACCCACGAT CTCGACGCCG TGCAGACCGG GGCGTGGATC 660
CTGCCCGACG AACGCCGAT TTCCGCTGAG CTGGAGGCGT TCCTGGACGC CGGCGCACCA 720
CCGGTGTACC TGGGGTTCGG CAGCCT- TCGC GCCCCCGCCG ACGCCGCGAA GGTGGC- CATC 780 GAGGCGATCC GTGCCCACGG CCAC- CGGGTG ATCCTCTCCC GCGGCTGGGC CGATCTGGTC 840
GTGCCCGACG ACCGGG- GAGGA CTGTTTCGCC ATCGGCGAAG TGAAT- CAGCA GGTGCTGTTC 900 CGCCGGGTGG CCGCCGTCAT CCACCACGGC GGCGCGGGCA CGACCCACGT GGCCACGCGG 960
GCGGGCGTCC CCCAGATCCT GTTCCCCAG ATCGCGGACC AGCCCTACTA CGCCGCCCGG 1020
GTGGCCGAAC TGGGGGTCGG TGTGGCG- CAT GACGGCCCGA CCCCGACCTT CGA- CACGTTG 1080 TCGGCGGCGC TCACCAAGGC CCTCGCTCCG GAAACGCGCG TGCGAGCGGA AGCCGTGGCG 1140
GAAACGGTCC AGACG- GACGG GGCCGCGGTG GCCGCGACC TGTTGT- TCGC CGCGGTGACC 1200 GGGAACCAGC CCGCCGTTCC CGCC 1224 which is SEQ ID NO:1;

(b) AUGCGUGUGU UGUUGUCGAC CUGUGG- GAGC CGCGGAGACG UCGAACCACU GGUG-

GCGUUG 60 GCGGUGCGGU UGCGGGAGCG CGGCGCCGAG GUGCGGAUGU GCGCGCCGCC GGACUGCGCG 120
GAUCGGCUGG CCGAAGUCGA CGUGCCGCAU CUGCCCCUCG GUGCGUCGGC GCGCCCGUCG 180
GCCGGGCAGG CGAAACCCUU GACGGCCGAG GACAUGCUCC GGUUCACGAC CGAGACGAUC 240
GCCACGCAGU UCGAGCGGAU UCCGGCG- GCC GCCGAAGGAU GCGCCGCGGU GGUGAC- GACC 300 GGCCUGCUGG CCGCCGCCAU CGGCGUGCGG UCGGUGGCCG AAAAGCUGGG CAUCCCCUAC 360
UUCUAUGGCU UCCA- CUGCCC GAGCUAUGUG CCGUCGCCGU ACUAUGCGCC UCCGCCGCCC 420 CUCGGC- GAGC CGCCCGCACC GGACGGGACC GACAUC- CAGG CGCUGUGGGA GCGCAACAAC 480
CAGAGCGCCU ACCGGCGGUA CGGGGAGCCG CUCAACAGCA GGCGCGCCGC CAUCGGCCUG 540
CCGCCGGUGG AGGCAAUCUU CGGC- CACGGC UACACCGAUC ACCCGUGGAU GGCG- GCGGAC 600 CCGGUACUGG CCCCGCUGCA ACCCACGGAU CUCGACGCCG UGCAGACCGG GGCGUGGAUC 660
CUGCCCGACG AACGAC- CGAU UUCCGCUGAG CUGGAGGCGU UCCUG- GACGC CGGCGCACCA 720 CCGGUGUACC UGGGGUUCGG CAGCCUUCGC GCCCCCGCCG ACGCCGCGAA GGUGGCCAUC 780 GAGGC- GAUCC GUGCCCACGG CCACGGGGUG AUCCU- CUCCC GCGGCUGGGC CGAUCUGGUC 840
CUGCCCGACG ACCGGGAGGA CUGUUUCGCC AUCGGCGAAG UGAAUCAGCA GGUGCUGUUC 900
CGCCGGGUGG CCGCCGUCAU CCAC- CACGGC GGCGCGGGCA CGACCCACGU GGC- CACGCGG 960 GCGGGCGUCC CCCAGAUCCU GGUUCCCCAG AUCGCGGACC AGCCCUACUA CGCCGCCCGG 1020
GUGGCCGAAC UGGGGGUCGG UGUGGCGCAU GACGGCCCGA CCCCGACCUU CGACACGUUG 1080
UCGGCGGCGC UCACCAAGGC CCUCGCUCCG GAACGCGCG UGCGAGCGGA AGCCGUGGCG 1140
GAAACGGUCC AGACGGACGG GGCCGCGGUG GCCGCGGACC UGUUGUUCGC CGCGGUGACC 1200
GGGAACCAGC CCGCCGUUCC CGCC 1224 which is SEQ ID NO:3;

(c) a nucleic acid compound complementary to (a) or (b).

4. An isolated nucleic acid compound comprising a sequence encoding the protein, wherein at amino acid position 335 of SEQ ID NO:2, Ser is substituted for Pro and wherein said compound has a sequence selected from the group consisting of:

(a) SEQ ID NO.1 wherein a "T" is substituted for a "C" at position 1003 and wherein a "T" is substituted for a "C" at position 1179;

(b) SEQ ID NO.3 wherein a "U" is substituted for a "C" at position 1003 and wherein a "U" is substituted for a "C" at position 1179;

(c) a nucleic acid compound complementary to (a) or (b).

5. An isolated nucletic acid compound of claim 3 wherein the sequence of said compound is SEQ ID NO:1 or a sequence complementary to SEQ ID NO:1.

6. An isolated nucleic acid compound of claim 3 wherein the sequence of said compound is SEQ ID NO:3 or a sequence complementary to SEQ ID NO:3.

7. A vector comprising an isolated nucleic acid compound of claim 3.

8. A vector comprising an isolated nucleic acid compound of claim 4.

9. A vector, as in claim 7, wherein said isolated nucleic acid compound is DNA operably linked to a promoter sequence.

10. A host cell containing the vector of claim 7.

11. A host cell containing the vector of claim 8.

12. A method for constructing a recombinant host cell having the potential to express SEQ ID NO:2, said method comprising introducing into said host cell by any suitable means a vector of claim 9.

13. A method for expressing SEQ ID NO:2 in the recombinant host cell of claim 12, said method comprising culturing said recombinant host cell under conditions suitable for gene expression.

* * * * *